US011369595B2

(12) United States Patent
Raynal et al.

(10) Patent No.: US 11,369,595 B2
(45) Date of Patent: Jun. 28, 2022

(54) USE OF TRYPTOPHAN METABOLITES FOR TREATING MUSCLE ATROPHY (71) Applicant: METABRAIN RESEARCH, Maisons-Alfort (FR)

(72) Inventors: Sophie N. Raynal, Paris (FR); Annick Audet, Leudeville (FR); Valérie Autier, Gif-sur-Yvette (FR); Christine Charon, Gometz le-Châtel (FR); Jean-Denis Durand, Montreuil sous Bois (FR); Micheline Kergoat, Les Ulis (FR)

(73) Assignee: METABRAIN RESEARCH, Les Ulis (FR)

( * ) Notice: Subject to any disclaimer, the term of this patent is extended or adjusted under 35 U.S.C. 154(b) by 0 days.

(21) Appl. No.: 16/329,281

(22) PCT Filed: Sep. 5, 2017

(86) PCT No.: PCT/FR2017/052338
§ 371 (c)(1),
(2) Date: Feb. 28, 2019

(87) PCT Pub. No.: WO2018/042141
PCT Pub. Date: Mar. 8, 2018

(65) Prior Publication Data
US 2019/0247385 A1 Aug. 15, 2019

(30) Foreign Application Priority Data

Sep. 5, 2016 (FR) ........................................ 1658239

(51) Int. Cl.
*A61K 31/47* (2006.01)
*A61P 21/00* (2006.01)
*A61K 9/00* (2006.01)

(52) U.S. Cl.
CPC ............ *A61K 31/47* (2013.01); *A61K 9/0053* (2013.01); *A61P 21/00* (2018.01)

(58) Field of Classification Search
CPC ................................ A61K 31/47; A61P 21/00
See application file for complete search history.

(56) References Cited

U.S. PATENT DOCUMENTS

| 5,270,309 A * | 12/1993 | Leeson | A61K 31/47 514/235.2 |
|---|---|---|---|
| 10,191,033 B2 * | 1/2019 | Thomas | A61K 38/00 |
| 10,350,184 B2 * | 7/2019 | Raynal | A61P 21/00 |
| 2006/0142241 A1 | 6/2006 | Too | |
| 2011/0110913 A1 | 5/2011 | Grant et al. | |
| 2011/0256132 A1 | 10/2011 | Ashman et al. | |
| 2015/0094289 A1 | 4/2015 | Gonzales et al. | |

FOREIGN PATENT DOCUMENTS

| CN | 101232878 A | 7/2008 | |
|---|---|---|---|
| CN | 102325793 A | 1/2012 | |
| CN | 104379136 A | 2/2015 | |
| EP | 2992879 A1 | 3/2016 | |
| JP | 2008-518935 A | 6/2008 | |
| JP | 2011-513338 A | 4/2011 | |
| JP | 2012-180331 A | 9/2012 | |
| JP | 2015-518887 A | 7/2015 | |
| RU | 2585372 C1 | 5/2016 | |
| WO | 2006050165 A2 | 5/2006 | |
| WO | 2006076580 A2 | 7/2006 | |
| WO | 2006/117624 A2 | 11/2006 | |
| WO | 2008087461 A2 | 7/2008 | |
| WO | 2009108999 A1 | 9/2009 | |
| WO | 2010/007085 A2 | 1/2010 | |
| WO | 2010070094 A1 | 6/2010 | |
| WO | 2013184591 A1 | 12/2013 | |
| WO | 2014026372 A1 | 2/2014 | |
| WO | WO-2016114655 A1 * | 7/2016 | ............. A61K 31/50 |

OTHER PUBLICATIONS

Turski et al., "Presence of kynurenic acid in food and honeybee products", 2009, Amino Acids, 26(1), pp. 75-80. (DOI 10.1007/s00726-008-0031-z) (Year: 2009).*
Silva-Adaya et al., "Protective effect of L-kynurenine and probenecid on 6-hydroxydopamine-induced striatal toxicity in rats: Implications of modulating kynurenate as a protective strategy", 2011, Neurotoxicology and Teratology, 33(2), pp. 303-312. (Year: 2011).*
Jeremy D. Walston, "Sarcopenia in older adults", 2012, Current Opinion in Rheumatology, 24(6), pp. 623-627. (Year: 2012).*
Cruz-Jentoft, Alfonso J et al., "Sarcopenia: revised European consensus on definition and diagnosis", 2019, Age and Ageing, 48(1), pp. 16-31. (Year: 2019).*
National Center for Biotechnology Information (2020). PubChem Compound Summary for CID 3845, Kynurenic acid. Create: Sep. 16, 2004. Retrieved Oct. 19, 2020 from https://pubchem.ncbi.nlm.nih.gov/compound/Kynurenic-acid. (Year: 2004).*
Turski et al., "Kynurenic Acid Content in Selected Culinary Herbs and Spices", Journal of Chemistry, vol. 2015, 2015, 7 pages; cited in the ISR.

(Continued)

*Primary Examiner* — My-Chau T. Tran
(74) *Attorney, Agent, or Firm* — Seckel IP, PLLC (57) ABSTRACT The present invention concerns a tryptophan metabolite chosen from kynurenic acid, anthranilic acid, quinolinic acid, picolinic acid, quinaldic acid and the mixtures of same or an enantiomer, diastereoisomer, hydrate, solvate, tautomer, racemic mixture or pharmaceutically acceptable salt of same, for use as a drug intended for increasing and/or maintaining muscle mass and/or strength in a mammal, and in particular intended for treating and/or preventing muscle atrophy in mammals and/or for promoting muscle growth in mammals doing exercise and aiming to increase muscle mass and/or quality and/or strength, for preventing the appearance of symptoms of sarcopenia or for rehabilitation following muscle loss and/or for improving recovery time after an intense physical effort.

24 Claims, 6 Drawing Sheets
Specification includes a Sequence Listing.

(56) References Cited

OTHER PUBLICATIONS

Walker et al., "Chromium picolinate effects on body composition and muscular performance in wrestlers", Medicine & Science in Sports & Exercise, vol. 30, No. 12, Dec. 1998, pp. 1730-1737; cited in the ISR.

Campbell et al., "Effects of resistance training and chromium picolinate on body composition and skeletal muscle in older men", Journal of Applied Physiology, vol. 86, No. 1, Jan. 1999, pp. 29-39; cited in the ISR.

Vincent, "The Potential Value and Toxicity of Chromium Picolinate as a Nutritional Supplement, Weight Loss Agent and Muscle Development Agent", Sports Medicine, vol. 33, No. 3, 2003, pp. 213-230; cited in the ISR.

Bass et al., "Growth factors controlling muscle development", Domestic Animal Endocrinology, vol. 17, 1999, pp. 191-197; cited in the Specification.

Bauer et al., "Evidence-Based Recommendations for Optimal Dietary Protein Intake in Older People: A Position Paper From the PROT-AGE Study Group", JAMDA, vol. 14, 2013, pp. 542-559; cited in the Specification.

Beyer et al., "Chronic low-grade inflammation and age-related sarcopenia", Current Opinion in Clinical Nutrition and Metabolic Care, vol. 15, No. 1, Jan. 2012, pp. 12-22; cited in the Specification.

Biolo et al., "Positive energy balance is associated with accelerated muscle atrophy and increased erythrocyte glutathione turnover during 5 wk of bed rest", The American Journal of Clinical Nutrition, vol. 88, 2008, pp. 950-958; cited in the Specification.

Biolo et al., "Muscle contractile and metabolic dysfunction is a common feature of sarcopenia of aging and chronic diseases: From sarcopenic obesity to cachexia", Clinical Nutrition, vol. 33, 2014, pp. 737-748; cited in the Specification.

Bosutti et al., "Calorie Restriction Modulates Inactivity-Induced Changes in the Inflammatory Markers C-Reactive Protein and Pentraxin-3", Journal of Clinical Endocrinol Metab, vol. 93, No. 8, Aug. 2008, pp. 3226-3229; cited in the Specification.

Caron et al., "A novel hindlimb immobilization procedure for studying skeletal muscle atrophy and recovery in mouse", Journal of Applied Physiology, vol. 106, Jun. 2009, pp. 2049-2059; cited in the Specification.

Deutz et al., "Protein intake and exercise for optimal muscle funtion with aging: Recommendations from the ESPEN Expert Group", Clinical Nutrition, vol. 33, 2014, pp. 929-936; cited in the Specification.

Donarski et al., "Identification of botanical biomarkers found in Corsican honey", Food Chemistry, vol. 118, Issue 4, Feb. 15, 2010, pp. 987-994; cited in the Specification.

Dukes et al., "The aromatic amino acid tryptophan stimulates skeletal muscle IGF1/p70s6k/mTor signaling in vivo and the expression of myogenic genes in vitro", Nutrition, vol. 31, 2015, pp. 1018-1024; cited in the Specification.

Guillet et al., "Impaired protein metabolism: interlinks between obesity, insulin resistance and inflammation", obesity reviews, vol. 13, Suppl. 2, Dec. 2012, pp. 51-57; cited in the Specification.

Guillet et al., "Changes in Basal and Insulin and Amino Acid Response of Whole Body and Skeletal Muscle Proteins in Obese Men", Journal of Clinical Endocrinol Metab, vol. 94, No. 8, Aug. 2009, pp. 3044-3050; cited in the Specification.

Lee, "Extracellular Regulation of Myostatin: A Molecular Rheostat for Muscle Mass" Immunology, Endocrine & Metabolic Agents in Medicinal Chemistry, vol. 10, No. 4, Dec. 2010, pp. 183-194; cited in the Specification.

Lin et al., "A Role for Tryptophan in Regulation of Protein Synthesis in Porcine Muscle", The Journal of Nutrition, vol. 118, Issue 4, Apr. 1, 1988, pp. 445-449; cited in the Specification.

McPherron et al., "Suppression of body fat accumulation in myostatin-deficient mice", The Journal of Clinical Investigation, vol. 109, No. 5, Mar. 2002, pp. 595-601; cited in the Specification.

Wolfman et al., "Activation of latent myostatin by the BMP-1/tolloid family of metalloproteinases", PNAS, vol. 100, No. 26, Dec. 23, 2003, pp. 15842-15846; cited in the Specification.

Sanfilippo et al., "Effects of a tryptophan deficient diet on the morphology of skeletal muscle fibers of the rat. Preliminary observations at neuroendocrinological and submicroscopical levels", Italian Journal of Anatomy and Embryology, vol. 100, Suppl. 1, 1995, 131-41; English abstract; cited in the Specification.

Turski et al., "Distribution, Synthesis, and Absorption of Kynurenic Acid in Plants", Planta Med, vol. 77, 2011, pp. 858-864; cited in the Specification.

Turski et al., "Potato—An Important Source of Nutritional Kynurenic Acid", Plant Foods for Human Nutrition, vol. 67, Issue 1, Mar. 2012, pp. 17-23; cited in the Specification.

Widner et al., "Simultaneous Measurement of Serum Tryptophan and Kynurenine by HPLC", Clinical Chemistry, vol. 43, Issue 12, Dec. 1997, 6 pages; cited in the Specification.

International Search Report and Written Opinion dated Jan. 2, 2018 issued in corresponding application No. PCT/FR2017/052338; w/ English partial translation and partial machine translation (23 pages).

Russian Search Report and Office Action dated Dec. 14, 2020 in corresponding application No. RU 2019109914; with English translation of Office Action (total 17 pages).

Lovelace et al., "Current Evidence for a Role of the Kynurenine Pathway of Tryptophan Metabolism in Multiple Sclerosis", Frontiers Immunology, 2016, vol. 7, No. 246, pp. 1-22 (in English) (D2 cited in the Russian Search Report).

Chinese Office Action and Search Report dated Dec. 3, 2021 in corresponding application No. CN201780054428.6 with English machine translation (total 17 pages) (WO2006117624A2 and WO2010007085A2, D4 and D6 cited in the Chinese Search Report are not listed in this IDS since they were already listed in the IDS filed Feb. 28, 2019).

Japanese Office Action dated Apr. 27, 2021 in corresponding application No. JP2019-533699; with English machine translation and summary (total 5 pages) WO2016114655, D4 cited in the Japanese Office Action is not listed in this IDS since it was already cited in the Office Action dated Oct. 22, 2020).

Iihama, "Idea: Thinking about Tryptophan Metabolism", Urinary Tract, vol. 17, No. 12, pp. 735-736, Dec. 1971; with English machine translation (total 6 pages) (D3 cited in the Japanese Office Action).

* cited by examiner

SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: mr myostatin d

<400> SEQUENCE: 1
gagtctgact ttctaatgca ag                                               22

<210> SEQ ID NO 2
<211> LENGTH: 20
<212> TYPE: DNA
<213> ORGANISM: Artificial Sequence
<220> FEATURE:
<223> OTHER INFORMATION: mr myostatin ind

<400> SEQUENCE: 2
tgttgtagga gtcttgacgg                                                  20

<210> SEQ ID NO 3
<211> LENGTH: 20
<212> TYPE: DNA
<213> ORGANISM: Artificial Sequence
<220> FEATURE:
<223> OTHER INFORMATION: mh Atrogin d

<400> SEQUENCE: 3
agagtcggca agtctgtgct                                                  20

<210> SEQ ID NO 4
<211> LENGTH: 19
<212> TYPE: DNA
<213> ORGANISM: Artificial Sequence
<220> FEATURE:
<223> OTHER INFORMATION: mh Atrogin ind

<400> SEQUENCE: 4
gtgaggcctt tgaaggcag                                                   19

<210> SEQ ID NO 5
<211> LENGTH: 20
<212> TYPE: DNA
<213> ORGANISM: Artificial Sequence
<220> FEATURE:
<223> OTHER INFORMATION: m beta-actin d

<400> SEQUENCE: 5
ctctagactt cgagcaggag                                                  20

<210> SEQ ID NO 6
<211> LENGTH: 19
<212> TYPE: DNA
<213> ORGANISM: Artificial Sequence
<220> FEATURE:
<223> OTHER INFORMATION: m beta-actin ind

<400> SEQUENCE: 6
ggtaccacca gacagcact                                                   19

USE OF TRYPTOPHAN METABOLITES FOR TREATING MUSCLE ATROPHY

DESCRIPTION OF THE INVENTION

The present invention relates to tryptophan metabolites of use for the treatment and prevention of muscle atrophy-related diseases.

FIELD OF THE INVENTION

From a functional point of view, it is important to dissociate muscle power involved in many basic activities (going from sitting to standing, going up stairs, walking) from sustained force (capacity to maintain a maximum level of contraction during a sustained effort) and from muscle quality (measure of force per unit of muscle mass) which can deteriorate as a function of situations, as in certain diseases associated with muscle fragility or atrophy (cachexia, sarcopenia, sarcopenic obesity, cancer, Duchenne muscular dystrophy (DMD), amyotrophic lateral sclerosis (ALS), myotonic dystrophy (MDA), heart failure, etc.), or during muscle traumas following an excessively intense physical effort. The coefficient of isokinetic endurance (ratio of force between the last three concentric muscle contractions relative to the first three) and the change in loss of muscle strength are generally good indicators regardless of the situation.

The aging of muscle function or muscle decline due to the gradual decrease in muscle mass and performance and/or strength, also referred to as sarcopenia, is responsible for significant complications such as an increase in the number of falls, a decrease in physical autonomy, immune system impairments. Multiple complex mechanisms are involved, such as inactivity, a decrease in physical activity, a poor nutritional state, an underlying inflammatory condition, but also hormonal and neurogenic factors, such as an imbalance between muscle protein degradation and synthesis which, in the end, result in muscle fiber atrophy and a reduction in the capacity to produce a force. These same mechanisms, the contribution of which varies according to the situation, are also found in the case of prolonged immobilization during cancer, heart or renal failure, or other serious chronic or acute diseases (cachexia, sarcopenic obesity, Duchenne muscular dystrophy (DMD), amyotrophic lateral sclerosis (ALS), myotonic dystrophy (MDA)), but also following a muscle trauma or a physical effort that is too intense.

In elderly individuals for example, when amino acids are diverted from the muscle, insulin resistance, the prevalence of which increases with age, plays an unfavorable role by increasing muscle protein proteolysis, resulting in a loss of muscle mass and strength (Bauer et al., 2013; Biolo et al., 2014). Likewise, the decrease in the level of anabolic hormones (testosterone, GH-IGF1, DHEA) like the increase in the level of pro-inflammatory cytokines (in particular IL-6 and TNF-α) amplify the proteolytic process (Bosutti et al., 2008; Biolo et al., 2008; Guillet et al., 2009). Moreover, the decrease in the activation of satellite cells responsible for muscle regeneration, the increase in the level of myostatin (or GDF-8) known to be expressed in skeletal muscle and to play an inhibitory role in muscle growth and development (Lee, 2010), of atrogin-1 (or MAFbx) and of MURF-1, mitochondrial aging and apoptosis (resulting in programmed cell death) also contribute to this phenomenon which may also be exacerbated by an increase in intramuscular fat in the case of sarcopenic obesity (Beyer et al., 2012). Conversely, genetic mutations in the myostatin gene, for example, increase skeletal muscle mass in animals, due to both a hyperplasic and a hypertrophic growth of myofibers (McPherron and Lee, 2002 and 2003; Bass et al., 1999).

While muscle strengthening can be at least partially compensated for by an increase in physical activity and by an additional intake of dietary proteins (Deutz et al., 2014), the prevention or treatment of sarcopenia is at the current time based solely on a program of regular physical activity adapted to each individual and monitoring of protein-energy intakes. The current recommendations recommend physical endurance (aerobic) activities, but also muscle strengthening (against resistance) activities, and also exercises which specifically call for balance. From a therapeutic point of view, testosterone and growth hormone (GH) improve muscle performances only for individuals with hypogonadism or who have a GH deficiency; DHEA unfortunately shows no benefit in terms of muscle performance; vitamin D decreases the risk of falling, without directly improving muscle strength or power. Thus, other lines of research are currently being carried out in order to define new therapeutic and preventive approaches. Certain selective androgen receptor modulators or SARMs, and also myostatin inhibitors, which are currently being studied, could prove to be beneficial like certain amino acids provided in the form of food supplements, in particular in malnourished elderly individuals.

Tryptophan (TRP) is an essential amino acid required for protein biosynthesis and is also the precursor of several biological molecules. Metabolized essentially by the kynurenine pathway (KP), tryptophan generates numerous metabolites (at least about a hundred), such as kynurenine (KYN), kynurenic acid (KA), anthranilic acid (AA), xanthurenic acid, quinolinic acid (QUIN), picolinic acid (PICO), quinaldic acid (QL-Dic), or 3OH-kynurenine in particular (Widner B et al., 1997), and also constitutes an important source for the de novo synthesis of $NAD^+$ or nicotinamide adenine dinucleotide.

It has been shown that TRP supplementation in mice subjected to a protein-poor diet is capable of reducing the loss of muscle mass by increasing the IGF-1 content in the muscles and modifying the expression of genes which play an important role in protein synthesis, muscle development or fiber size (Dukes A. et al., 2015), whereas the effect of L-kynurenine varies according to the dose tested (beneficial or negative). Former studies had already demonstrated the beneficial effect of TRP on muscle, its morphology, and protein synthesis (Sanfilippo et al., 1995; Lin et al., 1988).

However, no document either describes or suggests that tryptophan metabolites chosen from kynurenic acid, anthranilic acid, quinolinic acid, picolinic acid and quinaldic acid can have a positive effect on muscle mass. It has even, on the contrary, been proven in example 1 according to the invention that one of the tryptophan metabolites, 3OH-kynuerenin, has no effect on protein synthesis in C2C12 cells.

In the absence of efficacious treatments to date, it should be considered that individuals and more broadly mammals who exhibit a decrease in muscle performance and/or muscle strength/power might greatly benefit from drug treatments, enriched foods or food supplements intended to maximize muscle tissue anabolism and decrease muscle tissue catabolism.

While myostatin is a down-regulator of muscle development in several species, such as human beings, inhibition of the activity of the enzyme and of its expression in fact represents a therapeutic approach or intervention of interest for the treatment and prevention of muscle dysfunction.

DETAILED DESCRIPTION OF THE INVENTION

The present invention thus relates to one or more tryptophan (TRP) metabolites (also referred to as product according to the invention) chosen from kynurenic acid (KA), anthranilic acid (AA), quinolinic acid (QUIN), picolinic acid (PICO) and quinaldic acid (QL-Dic), and mixtures thereof, or an enantiomer, diastereoisomer, hydrate, solvate, tautomer, racemic mixture or pharmaceutically acceptable salt thereof, for use as a medicament intended for increasing and/or maintaining muscle mass and/or power in a mammal.

The most advantageous metabolite in the context of the present invention is kynurenic acid (KA), which can be used alone or in combination with one or more among anthranilic acid (AA), quinolinic acid (QUIN), picolinic acid (PICO) and quinaldic acid (QL-Dic).

In particular, the present invention relates to kynurenic acid (KA) or an enantiomer, diastereoisomer, hydrate, solvate, tautomer, racemic mixture or pharmaceutically acceptable salt thereof, for use as a medicament intended for increasing and/or maintaining muscle mass and/or power in a mammal.

It also relates to anthranilic acid (AA) or an enantiomer, diastereoisomer, hydrate, solvate, tautomer, racemic mixture or pharmaceutically acceptable salt thereof, for use as a medicament intended for increasing or maintaining muscle mass and/or power in a mammal.

It further relates to quinolinic acid (QUIN), or an enantiomer, diastereoisomer, hydrate, solvate, tautomer, racemic mixture or pharmaceutically acceptable salt thereof, for use as a medicament intended for increasing and/or maintaining muscle mass and/or power in a mammal.

It relates, moreover, to picolinic acid (PICO) or an enantiomer, diastereoisomer, hydrate, solvate, tautomer, racemic mixture or pharmaceutically acceptable salt thereof, for use as a medicament intended for increasing and/or maintaining muscle mass and/or power in a mammal.

It further relates to quinaldic acid (QL-Dic) or an enantiomer, diastereoisomer, hydrate, solvate, tautomer, racemic mixture or pharmaceutically acceptable salt thereof, for use as a medicament intended for increasing and/or maintaining muscle mass and/or power in a mammal.

Finally, it relates to a mixture of at least two products chosen from the group consisting of kynurenic acid (KA), anthranilic acid (AA), quinolinic acid (QUIN), picolinic acid (PICO) and quinaldic acid (QL-Dic), advantageously at least three products, in particular at least four products, more advantageously a mixture of all these products, or of an enantiomer, diastereoisomer, hydrate, solvate, tautomer, racemic mixture or pharmaceutically acceptable salt thereof, for use as a medicament intended for increasing and/or maintaining muscle mass and/or power in a mammal.

Advantageously, the metabolite(s)/product(s) according to the invention are intended for treating and/or preventing muscle atrophy in mammals and/or for limiting muscle atrophy in mammals and/or for promoting muscle growth in mammals performing exercise and aiming to increase muscle mass and/or quality and/or power, for preventing the appearance of symptoms of sarcopenia or for rehabilitation following muscle loss and/or for improving recovery time after an intense physical effort.

In particular, the muscle atrophy linked to age and/or to the consequences of a drug treatment and/or to a disease in connection with dystrophin abnormalities and/or to immobilization and/or to cachexia and/or to anorexia nervosa and/or to a situation of undernourishment and/or to dysphagia following pathological situations.

Advantageously, the muscle atrophy is pre-sarcopenia, sarcopenia or severe sarcopenia. Advantageously, the pre-sarcopenia, sarcopenia or severe sarcopenia is linked to aging, to obesity or to chronic diseases such as diabetes or heart failure.

In one particular embodiment, the muscle atrophy is linked to a disease in connection with dystrophin abnormalities, in particular chosen from Duchenne muscular dystrophy, Becker muscular dystrophy, amyotrophic lateral sclerosis and Steinert's myotonic dystrophy.

In yet another particular embodiment, the muscle atrophy is related to immobilization, in particular regardless of the cause, for example due to age-related weakness, to muscle traumas or to hospitalization (for example, post-fracture recovery, occurring pre-/post-bariatric surgery, burns), to an accident or to a surgical procedure, for instance insertion of a replacement knee or hip.

In another particular embodiment, the muscle atrophy is linked to cachexia, in particular cachexia associated with a chronic disease chosen from cancer, acquired immunodeficiency syndrome (AIDS), chronic obstructive pulmonary disease (COPD), heart failure, liver failure, tuberculosis, end-stage chronic renal disease (ESRD) and chronic inflammatory bowel diseases (IBDs).

In another particular embodiment, the muscle atrophy is linked to food behavior disorders such as anorexia nervosa.

In another particular embodiment, the muscle atrophy is linked to dysphagia following pathological situations (for example, post-stroke, Parkinson's disease, oculopharyngeal muscular dystrophy (OPMD)).

In particular, the mammal to whom the metabolite/product according to the invention is administered also suffers from metabolic diseases such as diabetes, obesity, non-alcoholic fatty liver disease (NAFLD) or non-alcoholic steatohepatitis (NASH), from chronic inflammatory bowel diseases (IBDs), from cancer, from renal or heart failure, from neurodegenerative pathological conditions or from psychiatric disorders such as depression.

Indeed, in the case where the mammal suffers from these metabolic diseases such as diabetes, obesity, non-alcoholic fatty liver disease (NAFLD) or non-alcoholic steatohepatitis (NASH), chronic inflammatory bowel diseases (IBDs), cancer, renal or heart failure, neurodegenerative pathological conditions or psychiatric disorders such as depression, the metabolite according to the invention will also have a favorable effect on this disease, apart from the effects described above.

The metabolite/product according to the invention is also of use for promoting muscle growth in mammals performing exercise and aiming to increase muscle mass and/or quality and/or power, for preventing for example the appearance of age-related symptoms of sarcopenia or for rehabilitation following muscle loss and/or for improving recovery time after an intense physical effort.

The mammal may be an animal (pet such as dog or cat) or other animal (cattle, members of the pig family, members of the sheep family, members of the goat family, members of the horse family) or a human being; it is advantageously a human being.

The inventors have discovered that the metabolites/products according to the present invention make it possible to increase protein synthesis in C2C12 muscle cells, to decrease myostatin gene expression in C2C12 muscle cells and/or to increase the diameter of C2C12 cell myotubes and therefore the size of these muscle fibers.

The present invention relates further to the use of a tryptophan metabolite/product according to the invention as defined above, for producing a medicament intended for increasing and/or maintaining muscle mass and/or power in a mammal and/or treating and/or preventing muscle atrophy in mammals and/or limiting muscle atrophy in mammals and/or for promoting muscle growth in mammals performing exercise and aiming to increase muscle mass and/or quality and/or power, for preventing the appearance of symptoms of sarcopenia or for rehabilitation following muscle loss and/or for improving recovery time after an intense physical effort.

Finally, it relates to a method for maintaining and/or increasing muscle mass and/or power in a mammal, for treatment and/or prophylactic treatment and/or for delaying the appearance of muscle atrophy in mammals and/or for limiting muscle atrophy in mammals and/or for promoting muscle growth in mammals performing exercise and aiming to increase muscle mass and/or quality and/or power, for preventing the appearance of symptoms of sarcopenia or for rehabilitation following muscle loss and/or for improving recovery time after an intense physical effort, comprising the administration of an effective amount of a tryptophan metabolite/product according to the invention to a subject requiring same.

The effective amount will be adjusted according to the nature and severity of the symptom to be treated, the route of administration and also the weight and age of the subject. In general, the average dose unit will vary between a dose of from 50 to 300 mg of metabolite/product, in particular of kynurenic acid (KA), per day in one or more intakes, when the subject is a human being.

The invention can thus be advantageously used in various situations of undernourishment, or situations associated with muscle fragility or atrophy: sarcopenia (linked to aging, to obesity or to chronic diseases such as diabetes or heart failure), cachexia associated with certain diseases (such as in particular cancer, acquired immunodeficiency syndrome (AIDS), chronic obstructive pulmonary disease (COPD), end-stage chronic renal disease (ESRD)), dysphagia following pathological situations (for example, post-stroke, Parkinson's disease, oculopharyngeal muscular dystrophy (OPMD), muscle traumas or hospitalization (for example, post-fracture recovery, occurring pre/post-bariatric surgery, burns), anorexia nervosa, rare diseases (such as Duchenne muscular dystrophy (DMD), amyotrophic lateral sclerosis (ALS), myotonic dystrophy (MD), etc.). The invention may also be used in sports medicine for improving for example recovery time after an intense physical effort, or as part of the composition of veterinary products for increasing muscle mass and/or quality in certain animals.

In one advantageous embodiment, the metabolite/product according to the invention is in a purified form, for example obtained by chemical synthesis, or in the form of a (crude or partially purified) plant extract obtained by methods well known to those skilled in the art (maceration, percolation, etc.) in a polar or organic solvent or a mixture thereof.

Indeed, tryptophan and metabolites thereof such as kynurenic acid for example are relatively abundant in conventional food or certain plants such as potato tubers, honeys, broccoli, medicinal herbs (Turski M P et al., 2011; Turski M P et al., 2012; Donarski et al., 2010).

Thus, it is possible to provide the beneficial dose of active metabolites of TRP/product according to the invention through the consumption of a food supplement or by ingestion foods (for example milk product or drink) enriched with an extract or natural or synthetic purified active substances.

Advantageously, the metabolite/product according to the invention is in the form of a pharmaceutical or veterinary composition comprising a pharmaceutically acceptable excipient. It may also be in the form of a nutraceutical composition or of a food supplement intended for oral administration.

In one advantageous embodiment, the pharmaceutical, veterinary or nutraceutical composition or the food supplement according to the present invention also comprises another active agent, advantageously having a complementary or synergistic effect.

This second active agent can be administered in the same pharmaceutical or nutraceutical or veterinary composition or the same food supplement as the metabolite of the present invention. It can also be administered separately, either at the same time or sequentially over time.

This active agent may be one or more medicaments or food supplements or foods or veterinary products or antibodies commonly used in the prevention or treatment of muscle dysfunction or the reduction of muscle mass, which could create useful pharmacological synergies with the metabolites according to the invention, depending on the situation (sarcopenia, sarcopenic obesity, heart or renal failure, anorexia, cachexia related to cancer or other chronic diseases, Duchenne muscular dystrophy (DMD), amyotrophic lateral sclerosis (ALS), myotonic dystrophy (MD), dysphagia related to certain pathological conditions, muscle traumas or hospitalizations, bariatric surgery, intense physical effort, etc.).

This active agent may correspond to nutritional products such as mixtures of proteins (such as creatine) or amino acids (such as for example lysine, arginine, leucine, beta-hydroxy-beta-methylbutyrate, citrulline), vitamins (such as vitamin D, B vitamins, etc.), minerals (such as magnesium, calcium, etc.), or other nutraceutical agents known for their anti-inflammatory properties (such as omega-3 polyunsaturated fatty acids (DHA, EPA)), or other active nutrients which facilitate its cellular action, such as phospholipids, for example phosphatidylcholine, phosphatidylserine).

This active agent may also correspond to certain hormones (such as growth hormone (GH), insulin-like growth factor (IGF-1)) for optimizing their effects and potentially reducing their side effects.

This active agent may also correspond to drug treatments (such as angiotensin II receptor antagonists, or selective androgenic receptor modulators (SARMs), or else myostatin inhibitors or antibodies).

This active agent may furthermore correspond to chondroprotective agents (such as glucosamine, chondroitin sulfate, hyaluronic acid, or collagen hydrolysates) with the aim of reinforcing the muscle mass impaired by immobility in individuals suffering from osteoarthritis.

Definitions

In the context of the present invention, the term "pharmaceutically acceptable" is intended to mean that which is useful in the preparation of a pharmaceutical or veterinary composition, which is generally safe, nontoxic and neither biologically undesirable nor undesirable in another way and which is acceptable for veterinary use as well as human pharmaceutical use.

In the context of the present invention, the expression "pharmaceutically acceptable salts of a metabolite or product" is intended to mean salts which are pharmaceutically acceptable, as defined herein, and which have the desired pharmacological activity of the parent metabolite. They are thus organic and inorganic addition salts of the acid and addition salts of bases) which are physiologically tolerated and produce no allergic or similar unfortunate reaction, such as dizziness, when they are administered to a human being or an animal. Examples of salts comprise, but without being limited thereto: acetate, adipate, alginate, aspartate, benzoate, benzenesulfonate, bisulfate, butyrate, citrate, camphorate, camphorsulfonate, cyclopentylpropionate, digluconate, dodecyl sulfate, ethanesulfonate, fumarate, flucoheptanoate, glycerophosphate, hemisulfate, heptanoate, hexanoate, hydrochloride, hydrobromide, hydriodide, 2-hydroxyethyl methanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts comprise the anions of the compounds of the present invention mixed with an appropriate cation, such as $Na^+$, $NH_4^+$, $NW_4^+$ (where W is a $C_1$-$C_4$ alkyl group), etc.

In the context of the present invention, the expression "solvate of a metabolite or product" is intended to mean any compound obtained by addition of a molecule of inert solvent to the metabolite/product according to the invention, the solvate forming because of their mutual attraction force. The solvates are for example alkoxides of the compound. A hydrate is a solvate in which the inert solvent used is water. It may be mono-, di- or trihydrated.

In the context of the present invention, the term "tautomer" is intended to mean any constitutional isomer of the metabolites according to the present invention which are interconvertible by the reversible chemical reaction known as tautomerization. In most cases, the reaction occurs by migration of a hydrogen atom accompanied by a change in location of a double bond. In a solution of a compound capable of tautomerization, an equilibrium between the two tautomers is created. The ratio between tautomers then depends on the solvent, the temperature and the pH. Tautomerism is thus the conversion of one functional group into another, usually by concomitant shift of a hydrogen atom and of a n bond (double or triple bond). Common tautomers are for example the following pairs: aldehydes/ketones-alcohols or more specifically enol; amides-imidic acids; lactams-lactims; imines-enamines; enamines-enamines. In particular, it may include a ring-chain tautomerism which takes place when the movement of the proton is accompanied by the conversion of an open structure to a ring.

The expression "excipient" means a nontoxic agent used in the formulation of pharmaceutical, nutraceutical or veterinary compositions or of a food supplement for providing a medium, and/or a form that can be used for a pharmaceutical, nutraceutical or veterinary composition or a food supplement. A carrier may comprise one or more of these agents, such as a stabilizer, or an aqueous solution at buffered pH. Examples of excipients which are pharmaceutically acceptable or can be used in a nutraceutical composition or a food supplement comprise aqueous or solid buffer ingredients, including phosphate, citrate and other organic acids; antioxidants comprising ascorbic acid; low-molecular-weight polypeptides (less than approximately 10 residues); proteins such as serum albumin, gelatin or immunoglobulins; hydrophilic polymers such as polyvinylpyrrolidone; amino acids such as glycine, glutamine, asparagine, arginine or lysine; monosaccharides; disaccharides and other carbohydrates comprising glucose, mannose or dextrins; chelating agents such as EDTA; sugar alcohols such as mannitol or sorbitol; salt-forming counterions, such as sodium; and/or nonionic surfactants such as Tween®, polyethylene glycol (PEG) and Pluronics®.

The pharmaceutical, nutraceutical or veterinary composition or the food supplement is prepared in order to be suitable for the administration mode. The acceptable pharmaceutical or nutraceutical excipients are determined partly by the composition administered, and also by the particular process used to administer the composition. Consequently, there is a large variety of suitable formulations of pharmaceutical, nutraceutical or veterinary compositions or of food supplements which could contain the metabolites/products which are described herein. The dosage of these metabolites/products to be administered depends on the individual case and, as usual, must be adjusted to the individual circumstances in order to obtain an effective therapeutic amount and an optimum effect. Thus, it depends on the nature and on the degree of severity of the ailment to be treated and also on the progression of the disease, and also on the age and general health condition of the patient and on the individual response of the human being or the animal to be treated. The daily dose can be administered in a single dose or, in particular when larger amounts are administered, can be divided into several individual doses.

The compositions can be in solid, liquid or semi-solid form, suitable for the various routes of administration (oral, rectal, nasal, intraocular, local—for example, topical, transdermal, buccal, vaginal or sublingual, or parenteral, for example subcutaneous, intramuscular, intravenous or intradermal). Oral administration is preferred; this route is the most suitable for chronic treatments. However, administration via other routes is possible, for example intravenously and transdermally. The intravenous formulations contain the active substance dissolved, in suspension or emulsified in a sterile carrier, optionally in the presence of emulsifying agents, stabilizers, buffering agents and other conventional additives; they are normally distributed into small bottles or flasks for infusion, and can be stored in the form of dry products to be reconstituted with water or with an appropriate carrier before use. The solid pharmaceutical compositions may be tablets, gel capsules, powders, granules, pills, powders to be reconstituted, etc.; they may contain conventional excipients such as binders, fillers, diluents, compression agents, lubricants, detergents, dyes, flavoring agents and wetting agents. The tablets may be coated in accordance with methods well known in the technical field. Suitable fillers comprise cellulose, mannitol, lactose and other similar agents. The liquid compositions for oral administration may be in the form of aqueous or oily suspensions, solutions, emulsions, syrups or elixirs or may be present in the form of dry products for reconstitution with water or a suitable carrier before use; they may contain conventional additives, for example suspending agents such as sorbitol, syrup, methylcellulose, gelatin, hydroxyethylcellulose, carboxymethylcellulose, a gel of aluminum stearate or hydrogenated edible fats, emulsifiers such as lecithin, sorbitan monooleate or gum arabic; nonaqueous transporters (which may comprise edible oils) such as almond oil, fractionated coconut oil, oily esters such as esters of glycerol, of propylene glycol or of ethyl alcohol; preservatives such as methyl or propyl p-hydroxybenzoate or sorbic acid and, if desired, conventional flavoring or coloring agents.

The term "prevention" refers to a reduction in the risk of contracting or developing a disease or a disorder (for example, making sure that at least one of the clinical symptoms of the disease cannot develop) in a subject who may be exposed to a pathogenic agent, or predisposed to the disease before its appearance.

The term "treatment" of a disease or of a disorder denotes, in one embodiment, the improvement of the disease or disorder (for example, by arresting the disease or reducing the manifestation, the extent or the seriousness of at least one of the clinical symptoms thereof).

The natural or synthetic molecules may be used in combination with a suitable pharmaceutical support. Such compositions comprise an effective amount of the TRP metabolites or product according to the invention, and an acceptable pharmaceutical support or an excipient.

The invention will be understood more clearly on reading the description of the figures and examples which follow, which are given purely by way of nonlimiting indication.

FIG. 7 represents the effect of kynurenic acid on the morphometric parameters of C2C12 muscle fibers (FIGS. 7A-B).

EXAMPLE 1: MEASUREMENT OF PROTEIN SYNTHESIS IN C2C12 CELLS

The cells are counted and seeded at the density of 20 000 cells per well in a 24-well plate in DMEM medium containing glucose in a proportion of 4.5 g/l and supplemented with fetal calf serum (10%) and with antibiotics (penicillin and streptomycin). Forty-eight hours layer, the myoblasts are induced to differentiate by partial serum deprivation (2% instead of 10%) for 5 days. The cells are then placed in medium without glucose or leucine (Krebs medium) for 1 h at 37° C., then incubated for 150 min in the presence of the products to be tested (DMSO (control), kynurenic acid or anthranilic acid or quinolinic acid or picolinic acid or 3OH-kynurenine) or reference (IGF-1, 100 ng/ml) in serum-free DMEM medium containing 2.5 µCi/ml radio-labeled leucine. At the end of the incubation, the supernatants are removed and the cells are lysed in 0.1N NaOH solution for 30 min. The radioactivity is measured in the cell fraction and the total amount of proteins is determined by assaying according to the Lowry method. Each condition is evaluated at least with n=6; IGF-1, 100 ng/ml is our control for stimulating protein synthesis. The results are expressed in cpm/µg of proteins after 150 min of incubation or as a percentage relative to the control condition. The results are expressed as % of the control and a statistical test is carried out: Dunnett's or Dun test (*p<0.05, p<0.01, *p<0.001 versus control). The results obtained with kynurenic acid, anthranilic acid, quinolinic acid, picolinic acid and 3OH-kynurenin are represented in FIGS. 1 to 5. They show that kynurenic acid, anthranilic acid, quinolinic acid and picolinic acid significantly induce protein synthesis. A dose-dependent stimulation of protein synthesis is observed after 150 min of incubation in the presence of kynurenic acid. On the other hand, 3OH-kynureninin, another tryptophan metabolite, has no effect on protein synthesis.

EXAMPLE 2: MEASUREMENT OF MYOSTATIN GENE EXPRESSION IN C2C12 CELLS

The C2C12 myoblast cells (ATCC CRL-1772) are seeded in 24-well plates at the density of 30 000 cells per well and cultured in a DMEM medium containing glucose in a proportion of 4.5 g/l and supplemented with fetal calf serum (10%) and with antibiotics (penicillin and streptomycin). Forty-eight hours later, the myoblasts are induced to differentiate by partial serum deprivation (2% instead of 10%) for 5 days. The cells are then placed in a serum-free, glucose-depleted medium (DMEM containing 1 g/l of glucose) in the presence of the molecules to be tested (DMSO (control) or IGF-1 (100 ng/ml) or kynurenic acid) or of the references (IGF-1 at the concentration of 100 ng/ml) for 6 h. At the end of the experiment, the messenger RNAs (mRNAs) are extracted using the conventional methodology based on phenol and chloroform. Briefly, the cells are lysed in a trizol solution (Sigma T9424) containing a strong acid and phenol. The mRNAs are separated from the proteins by addition of chloroform and then centrifugation. They are then precipitated from isopropanol so as to then be suspended at the concentration of 1 µg/µl in an RNase-free and DNAse-free ultrapure water. 1 µg of mRNA is then converted by reverse transcription into complementary DNA using the AMV enzyme in the presence of a primer and of a mixture of nucleotides according to the protocol given by the supplier (Applied Biosystems 4368814). The gene expression is studied by polymerase chain reaction, commonly referred to as PCR, under quantitative conditions, hence the specific name qPCR. The qPCRs are carried out on a 7900HT Fast real-Time PCR detection system (Applied Biosystems). The programming conditions are standard and consist of 1 cycle at 95° C. for 15 min, followed by 40 cycles at 95° C. for 15 s and at 60° C. for 1 min and ending with a melting curve step between 60° C. and 95° C. The samples analyzed all contain 100 mg of cDNA, a qPCR buffer including the enzyme, the oligonucleotide mixture and the intercalating agent (sybergreen), and the pair of primers specific for the gene studied, strategically chosen between two exon sequences and at the final concentration of 200 nM. Fluorescent probes bind to the double-stranded DNA and fluoresce only once bound to the DNA. A fluorescence threshold is established by the program of the machine. When the amount of DNA allows the fluorescent probe to exceed this threshold, a PCR cycle number called "Ct" for "Cycle Threshold" is obtained. It is this value which forms the basis for the calculations to relatively quantify the DNA. A ratio R is established between the amount of starting DNA of a sample and that of a control, which has not undergone treatment (i.e. $R=2^{-(Ct\ sample-Ct\ control)}$), and this measure ment which is related back to that of a housekeeping gene known not to be modulated by the treatment (i.e. $R=2^{-\Delta\Delta Ct}$).

The primers used are given in table 1 below:

TABLE 1

Primers used to evaluate the gene expression modifications

| Gene | Sequence 5'→3' | No. of bases | Tm | Acession number |
|---|---|---|---|---|
| mr myostatin d | GAGTCTGACTTTCTAATGCAAG | 21 | 62 | m: NM_010834 |
| mr myostatin ind | TGTTGTAGGAGTCTTGACGG | 20 | 60 | r: AF019624 |
| mh Atrogin d | AGAGTCGGCAAGTCTGTGCT | 20 | 62 | m: AF441120 |
| mh Atrogin ind | GTGAGGCCTTTGAAGGCAG | 19 | 60 | h: NM_058229 |
| m beta-actin d | CTCTAGACTTCGAGCAGGAG | 20 | 62 | m: X03672 |
| m beta-actin ind | GGTACCACCAGACAGCACT | 19 | 60 | |

Figure 1:
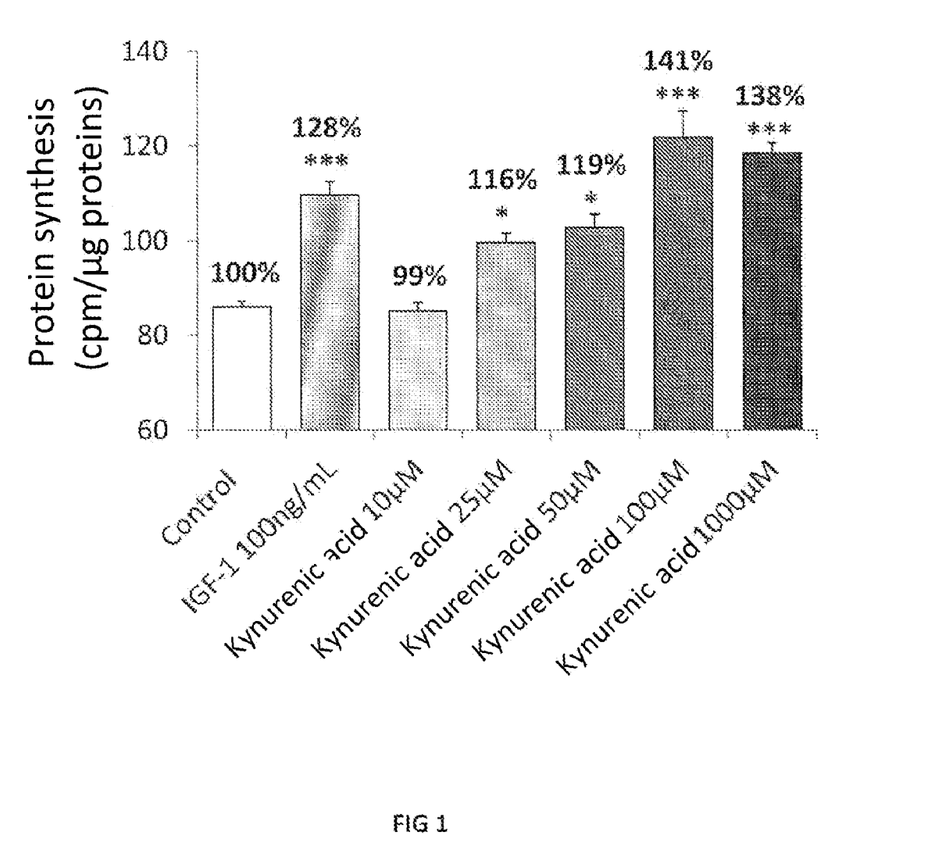
FIG. 1 represents the effect of kynurenic acid (KA) on protein synthesis in C2C12 muscle cells as a function of the dose used.
Figure 2:
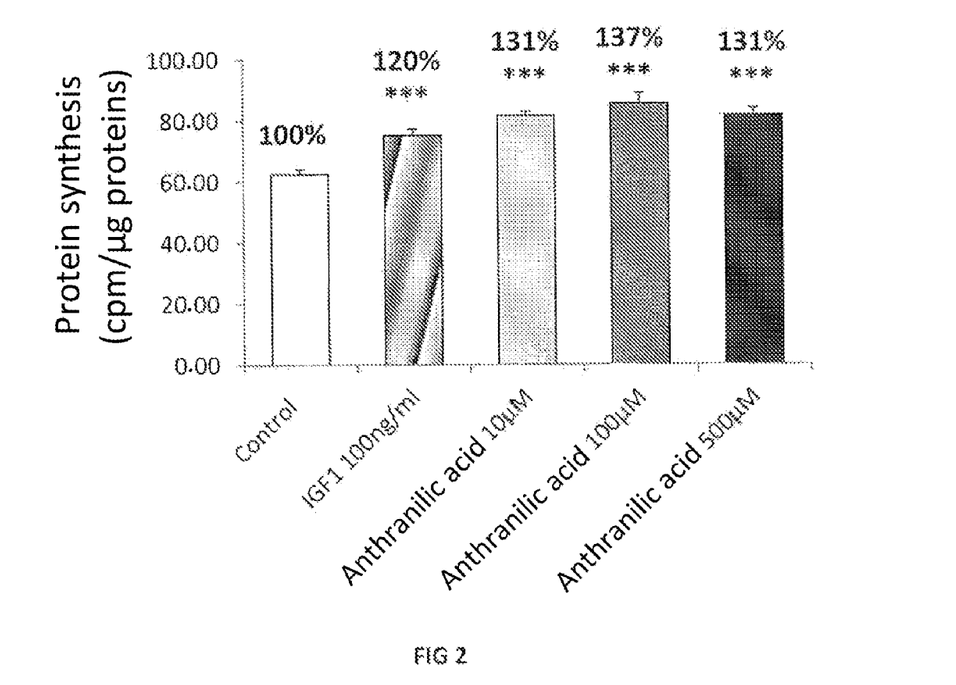
FIG. 2 represents the effect of anthranilic acid on protein synthesis in C2C12 muscle cells.
Figure 3:
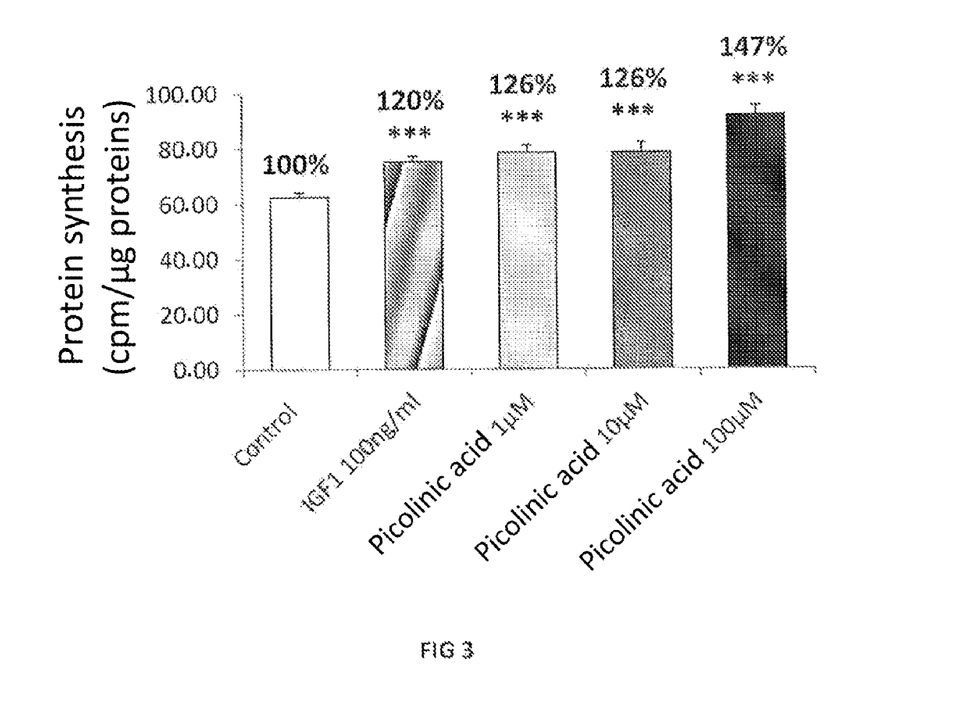
FIG. 3 represents the effect of quinolinic acid on protein synthesis in C2C12 muscle cells.
Figure 4:
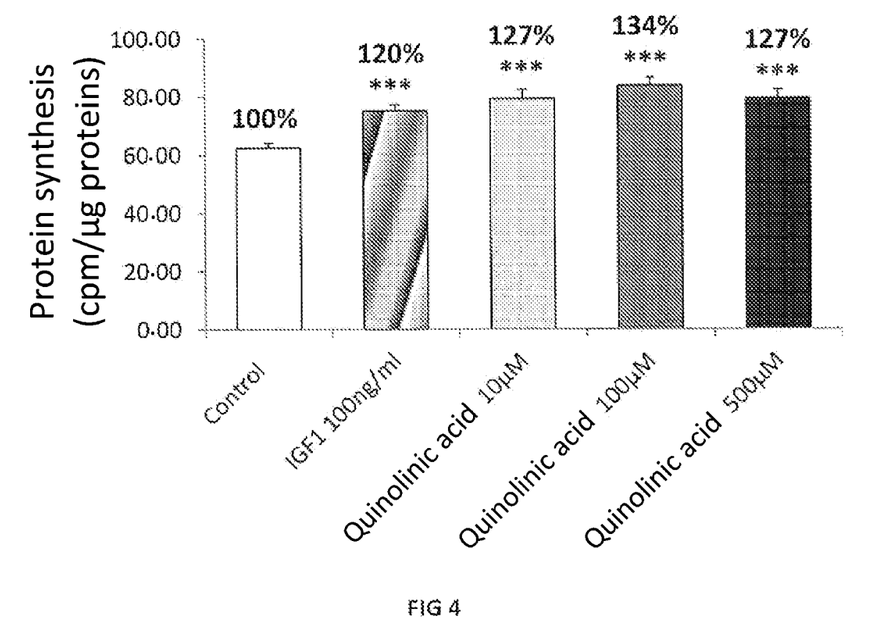
FIG. 4 represents the effect of picolinic acid on protein synthesis in C2C12 muscle cells.
Figure 5:
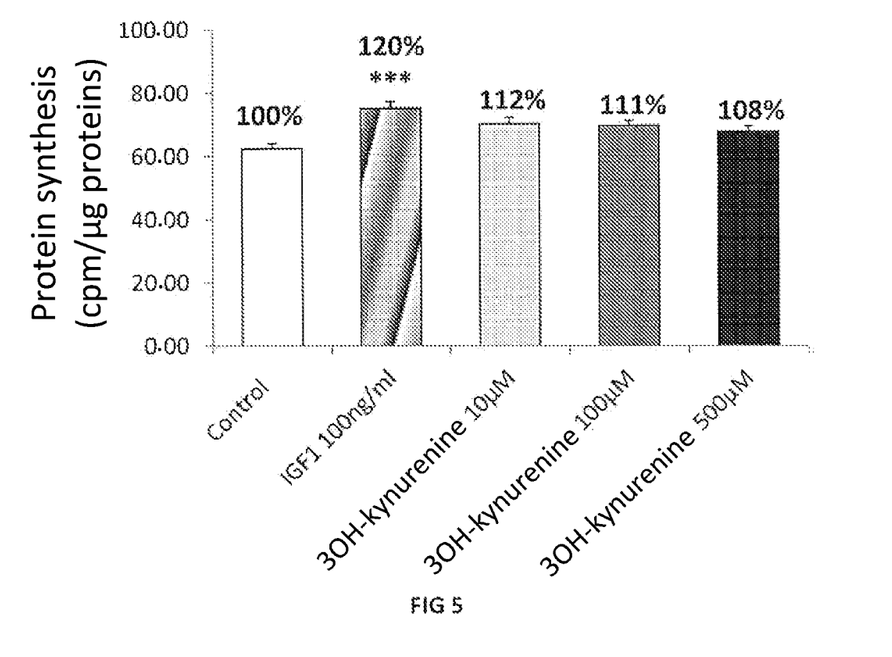
FIG. 5 represents the effect of 3OH-kynurenine on protein synthesis in C2C12 muscle cells.
Figure 6:
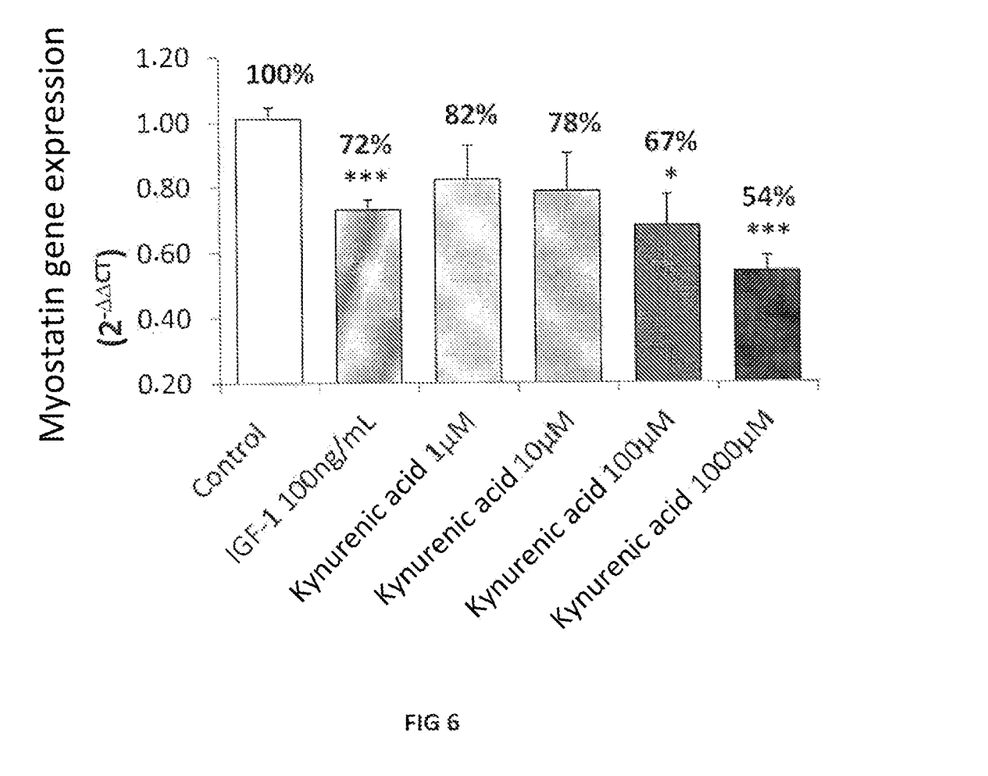
FIG. 6 represents the effect of kynurenic acid on myostatin gene expression in C2C12 muscle cells.

At the end of the incubation, the expression of the myostatin gene is measured by RT-qPCR and standardized using the beta-actin housekeeping gene. A statistical test is carried out: Dunnett's or Dun test (*p<0.05, p<0.01, *p<0.001 versus control). The results obtained with kynurenic acid are represented in FIG. 6. A significant dose-dependent inhibition of myostatin gene expression is observed after 6 hours of incubation with kynurenic acid.

EXAMPLE 3: EVALUATION OF THE DIAMETER OF THE C2C12 MUSCLE FIBERS

Figure 7A:
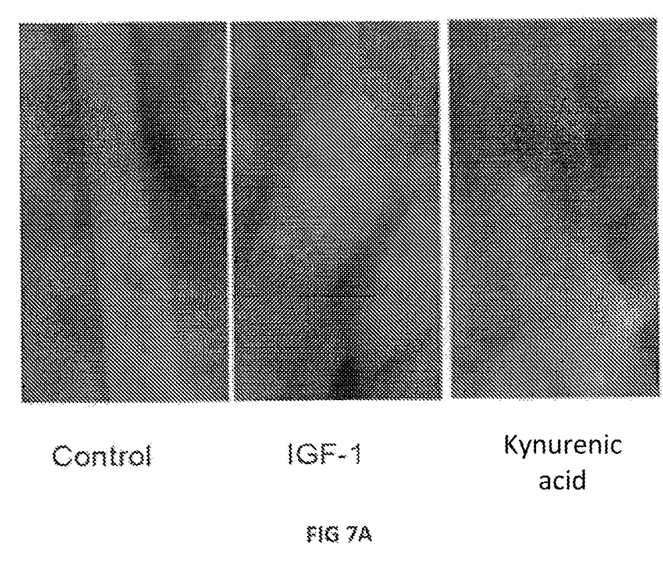
Figure 7B:
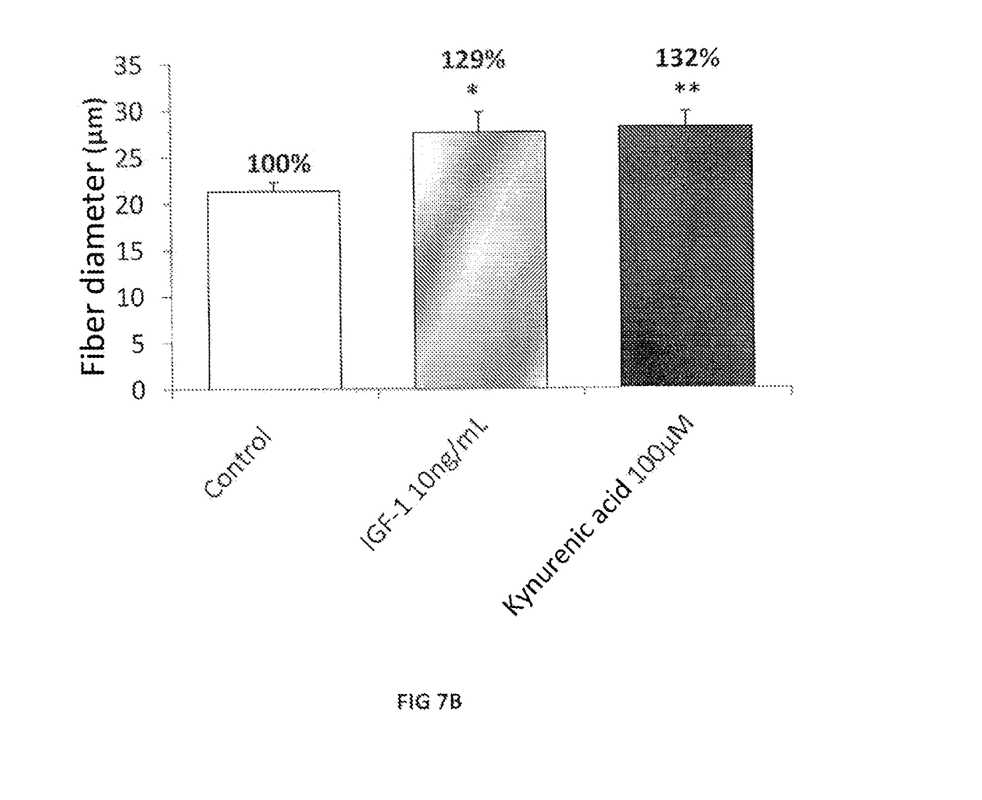

The C2C12 myoblast cells (ATCC CRL-1772) are seeded in 8-well plates treated with glycerol, at the density of 10 000 cells per well and cultured in DMEM medium containing glucose in a proportion of 4.5 g/l and supplemented with fetal calf serum (10%) and with antibiotics (penicillin and streptomycin). Forty-eight hours layer, the myoblasts are induced to differentiate by partial serum deprivation (2% instead of 10%) for 3 days. The cells are then placed in a serum-free, glucose-depleted medium (DMEM containing 1 g/l of glucose) in the presence of the molecules to be tested (DMSO (control) or kynurenic acid) or the references (IGF-1 at the concentration of 10 ng/ml or dexamethasone at 10 µM) for 3 days. At the end of the culture, the cells are rinsed and fixed using a 2.5% glutaraldehyde/0.1% triton solution for 1 h at ambient temperature. The cell layer is covered with DAPI (fluorescent labeling of the cell nucleus). After storage in the dark for 16 h in the cold, the slides are observed under a fluorescence microscope (Carl Zeiss, AxioVert 200) and the images are analyzed using the Axiovision 4.1 software for measuring the diameter of the fibers. A representative image of each condition is shown. A statistical test is carried out: Dunnett's or Dun test (*p<0.05, p<0.01, *p<0.001 versus control). The results obtained with kynurenic acid are represented in FIG. 7. After incubation for 3 days in the presence of kynurenic acid (100 µM), an increase in the size of the C2C12 muscle fibers is observed.

EXAMPLE 4: EFFECT OF KYNURENIC ACID ON MUSCLE ATROPHY INDUCED BY IMMOBILIZATION IN MICE

Figure 8:
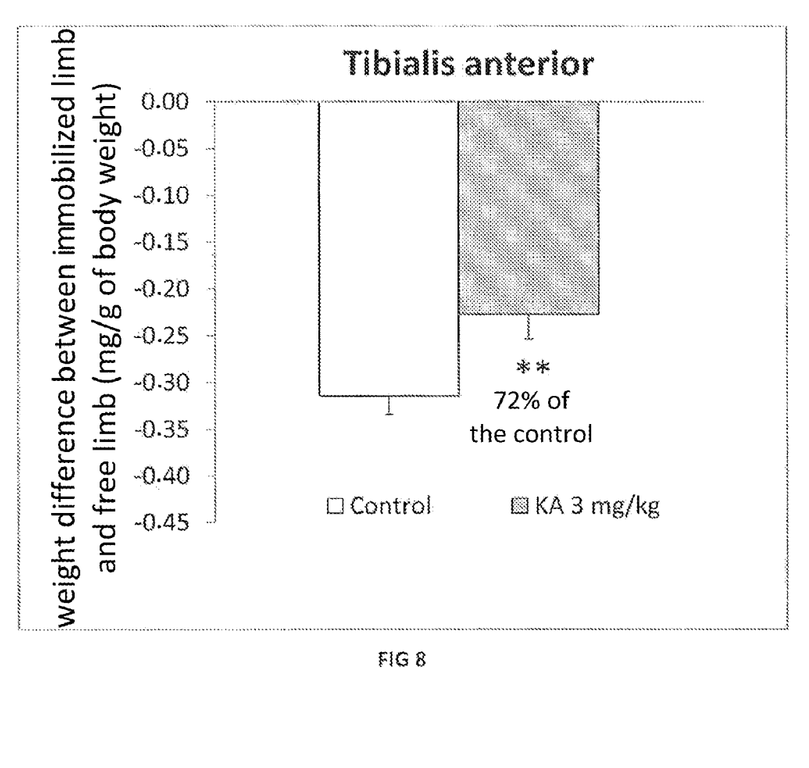
FIG. 8 represents the effect of kynurenic acid on muscle atrophy induced by immobilization for 7 days in normal mice.

Limb immobilization is known to induce skeletal muscle atrophy involving mechanisms linked to protein degradation, to a change in muscle fiber types, to oxidative stress or inflammatory mechanisms. Briefly, male 8-9-week-old CD1 mice were used in this study. The foot of the left hindlimb was immobilized for 7 days according to the procedure described by Caron et al. (2009), in the dorso-tibial flexion position, by means of a surgical staple. The other foot (right hindlimb) is used as a control. For the duration of the immobilization, one group of animals (n=12) received a treatment with kynurenic acid (3 mg/kg per day) in the drinking water. Another group of animals served as a control (n=16 animals). At the end of the 7 days of study, the animals were sacrificed in order to remove the Tibialis anterial muscle from the two hindlimbs. For each animal, the difference between the weight of the muscle of the immobilized limb and the free limb is calculated, then related back to the bodyweight. The results are expressed as weight loss of the immobilized limb relative to the control limb (in mg per g of body weight), and a statistical test is carried out: Student's test (*p<0.05, p<0.01, *p<0.001 versus control group). The results obtained show that kynurenic acid significantly decreases the loss of muscle (Tibialis anterior) mass induced by immobilization, compared with the control group without treatment (FIG. 8).

LITERATURE

Bass J et al., Domest Anim Endocrinol, 1999, 17 (2-3): 191-197
Bauer J et al., J Am Med Dir Assoc, 2013, 14: 542-559
Beyer et al., Curr. Opin. Clin. Nutr. Metab. Care, 2012, 15: 12-22
Biolo G et al., Am J Clin Nutr, 2008, 88: 950-958
Biolo et al., Clinical Nutrition, 2014, 33: 737-748
Bosutti A et al., J Clin Endocrinol Metab, 2008, 93: 3226-3229
Caron A Z et al. J Appl Physiol. 2009; 106: 2049-2059
Deutz N E et al., Clin Nutr, 2014, 33(6): 929-36
Donarski J. A. et al. Food Chemistry, 2010, 118: 987-994
Dukes A. et al., Nutrition, 2015, 31: 1018-1024
Guillet C et al., Obes Rev, 2012, 13 (Suppl. 2): 51-57
Guillet C et al., J Clin Endocrinol Metab, 2009, 94: 3044-3050
Lee S J. Immunol Endocr Metab Agents Med Chem., 2010, 10: 183-194
Lin F D, et al., J Nutr., 1988, 118: 445-449
McPherron A C et al., J Clin Invest. 2002, 109: 595-601
McPherron A C and Lee, Proc. Natl. Acad. Sci. USA 2003, 100 (260): 15842-15846
Sanfilippo et al., Ital J Anat Embryol, 1995, 100: 131-141
Turski M. P., et al. Planta Med., 2011, 77: 858-864
Turski M. P. et al. Plant Foods Hum Nutr, 2012, 67:17-23
Widner B et al., Clinical Chemistry, 1997, 43: 2424-26

The invention claimed is:

1. A method of increasing and/or maintaining muscle mass and/or power in a mammal, comprising administering to the mammal at least one tryptophan metabolite selected from the group consisting of kynurenic acid, enantiomers of kynurenic acid, diastereomers of kynurenic acid, hydrates of kynurenic acid, solvates of kynurenic acid, tautomers of kynurenic acid, racemic mixtures of kynurenic acid, and pharmaceutically acceptable salts thereof;
    wherein the muscle atrophy is pre-sarcopenia, sarcopenia or severe sarcopenia.

2. The method as claimed in claim 1, which is a method of treating and/or preventing muscle atrophy in mammals, and/or limiting muscle atrophy in mammals, and/or promoting muscle growth in mammals performing exercise and aiming to increase muscle mass and/or quality and/or power, and/or treating and/or preventing the appearance of symptoms of sarcopenia, and/or rehabilitation following muscle loss, and/or improving recovery time after an intense physical effort.

3. The method as claimed in claim 2, which is a method of treating and/or preventing muscle atrophy in mammals, wherein the muscle atrophy is related to age and/or to the consequences of a drug treatment and/or to a disease in connection with dystrophin abnormalities and/or to immobilization and/or to cachexia and/or to anorexia nervosa and/or to a situation of undernourishment and/or to dysphagia following pathological situations.

4. The method as claimed in claim 1, which is a method of preventing and/or treating the appearance of symptoms of sarcopenia, wherein the symptoms include symptoms of pre-sarcopenia, sarcopenia or severe sarcopenia related to aging, to obesity and/or to chronic diseases.

5. The method as claimed in claim 3, wherein the muscle atrophy is related to a disease in connection with dystrophin abnormalities, and wherein the disease in connection with dystrophin abnormalities is selected from the group consisting of Duchenne muscular dystrophy, Becker muscular dystrophy, amyotrophic lateral sclerosis and Steinert's myotonic dystrophy.

6. The method as claimed in claim 3, wherein the muscle atrophy is related to cachexia, and wherein the cachexia is associated with a disease selected from the group consisting of cancer, acquired immunodeficiency syndrome (AIDS), chronic obstructive pulmonary disease (COPD), heart failure, liver failure, tuberculosis, end-stage chronic renal disease (ESRD) and chronic inflammatory bowel diseases (IBDs).

7. The method as claimed in claim 1, wherein the mammal is also suffering from a disease selected from the group consisting of metabolic diseases, chronic inflammatory bowel diseases (IBDs), cancer, renal or heart failure, neurodegenerative pathological conditions and psychiatric disorders.

8. The method as claimed in claim 1, wherein the mammal is a human being.

9. The method as claimed in claim 1, wherein the at least one tryptophan metabolite is in a purified form.

10. The method as claimed in claim 1, wherein the at least one tryptophan metabolite is in the form of a pharmaceutical or veterinary composition comprising a pharmaceutically acceptable excipient.

11. The method as claimed in claim 1, wherein the at least one tryptophan metabolite is in the form of a nutraceutical composition or of a food supplement intended for oral administration.

12. The method as claimed in claim 10, wherein the composition is in the form of a pharmaceutical or veterinary composition adapted to be administered orally.

13. The method as claimed in claim 1, wherein the at least one tryptophan metabolite is administered orally.

14. The method as claimed in claim 1, wherein the at least one tryptophan metabolite is kynurenic acid or a pharmaceutically acceptable salt thereof.

15. The method as claimed in claim 4, wherein the symptoms are related to a chronic disease which is diabetes or heart failure.

16. The method as claimed in claim 7, wherein the mammal is suffering from at least one metabolic disease selected from the group consisting of diabetes, obesity, non-alcoholic fatty liver disease (NAFLD), and non-alcoholic steatohepatitis (NASH).

17. The method as claimed in claim 7, wherein the mammal is suffering from a psychiatric disorder which is depression.

18. The method as claimed in claim 2, which is a method of treating and/or preventing muscle atrophy in mammals, and/or limiting muscle atrophy in mammals.

19. The method as claimed in claim 1, wherein the mammal is an animal, which is a pet.

20. The method as claimed in claim 1, wherein the mammal is selected from the group consisting of cattle, members of the pig family, members of the sheep family, members of the goat family, and members of the horse family.

21. The method as claimed in claim 9, wherein the at least one tryptophan metabolite has been obtained by chemical synthesis.

22. The method as claimed in claim 1, wherein the at least one tryptophan metabolite is in the form of a plant extract.

23. The method as claimed in claim 3, wherein the muscle atrophy is related to a dysphagia following a pathological situation, wherein the pathological situation is a post-stroke situation, Parkinson's disease, or oculopharyngeal muscular dystrophy (OPMD).

24. The method as claimed in claim 1, wherein the at least one tryptophan metabolite is administered in an amount effective to provide at least one of the following effects in muscles cells of the mammal: (i) increase protein synthesismal, (ii) decrease myostatin gene expression, (iii) increase a diameter of myotubes.

* * * * *